United States Patent [19]

Le Roy et al.

[11] Patent Number: 4,960,904

[45] Date of Patent: Oct. 2, 1990

[54] PROCESS FOR THE PREPARATION OF CYCLIC SULPHATES

[75] Inventors: Pierre Le Roy, Lyons; Bernadette Mandard-Cazin, Alfortville, both of France

[73] Assignee: Rhone-Poulenc Sante, Antony, France

[21] Appl. No.: 403,444

[22] Filed: Sep. 6, 1989

Related U.S. Application Data

[63] Continuation-in-part of Ser. No. 319,190, Mar. 6, 1989, abandoned.

[30] Foreign Application Priority Data

Mar. 8, 1988 [FR] France .................. 88 02917

[51] Int. Cl.$^5$ .......................................... C07D 327/10
[52] U.S. Cl. .................................................. 549/34
[58] Field of Search ..................................... 549/18, 34

[56] References Cited

PUBLICATIONS

*J. Chem. Soc., Chem. Commun.*, 1983, pp. 1392–1394.
*Chem. Abstracts*, vol. 108, 1998, Abst. No. 37493n.

Primary Examiner—Mary C. Lee
Assistant Examiner—M. S. Howard
Attorney, Agent, or Firm—Stevens, Davis, Miller & Mosher

[57] ABSTRACT

Cyclic sulphates of formula:

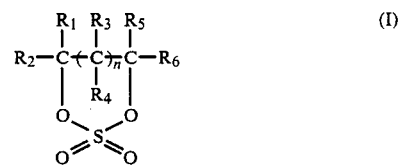

are prepared by oxidation of a cyclic sulphite of formula:

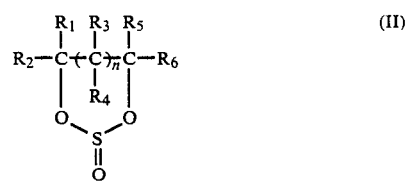

with a hypohalite of an alkali or alkaline-earth metal and a catalytic quantity of a ruthernium derivative ($RuO_2$, $RuCl_3$). In formulae (I) and (II), $R_1$, $R_2$, $R_3$, $R_4$, $R_5$ and $R_6$ are identical or different and each represents hydrogen, halogen, alkyl, alkoxy, aryl, aryloxy or alkoxycarbonyl.

1 Claim, No Drawings

PROCESS FOR THE PREPARATION OF CYCLIC SULPHATES

This Application is a Continuation-in-Part of our application Ser. No. 319,190 filed Mar. 6th, 1989, now abandoned.

The present invention relates to the preparation of cyclic sulphates of formula:

$$\begin{array}{c} R_1 \ \ R_3 \ \ R_5 \\ | \ \ \ | \ \ \ | \\ R_2-C+C\!\!\rightarrow_{\!n}\!C-R_6 \\ | \ \ \ | \\ \ \ \ R_4 \\ O \diagdown \ \ \diagup O \\ S \\ O \diagup \ \ \diagdown O \end{array} \quad (I)$$

by oxidation of cyclic sulphites of formula:

$$\begin{array}{c} R_1 \ \ R_3 \ \ R_5 \\ | \ \ \ | \ \ \ | \\ R_2-C+C\!\!\rightarrow_{\!n}\!C-R_6 \\ | \ \ \ | \\ \ \ \ R_4 \\ O \diagdown \ \ \diagup O \\ S \\ \| \\ O \end{array} \quad (II)$$

in which $R_1$, $R_2$, $R_3$, $R_4$, $R_5$ and $R_6$ are identical or different and each represents hydrogen, halogen, alkyl, aryl, alkoxy, aryloxy or alkoxycarbonyl and n is 0 or 1, the said alkyl radicals and alkyl portions of alkoxy or alkoxycarbonyl radicals containing 1 to 4 carbon atoms each and being unsubstituted or substituted by one or more identical or different atoms or radicals selected from halogen, e.g. chlorine, alkoxy, aryloxy or alkoxycarbonyl, the said aryl radicals and the aryl portions of the aryloxy radicals containing 6 to 10 carbon atoms each and being unsubstituted or substituted by one or more identical or different atoms or radicals selected from halogen, alkyl, alkoxy, aryloxy or alkoxycarbonyl.

The compounds of formula (I) are useful intermediates in organic chemistry, in particular for performing hydroxyalkylation reactions. The product 1-chloromethylethylene sulphate (or 3-chloro-1,2-propanediol sulphate) is a new compound.

It is known, in particular from the article by G. Lowe and S. J. Salamone, J. Chem. Soc., Chem. Comm., 1392-1394 (1983), that cyclic sulphates of formula (I) may be obtained by oxidation of cyclic sulphites of formula (II) using ruthenium tetroxide prepared in situ from ruthenium oxide ($RuO_2$) and sodium periodate. However the performance of this process requires the use of ruthenium (IV) oxide in stoichiometric quantities and of sodium periodate both of which are expensive.

It has now been found, and this consitutes the subject of the present invention, that the oxidation of cyclic sulphites of formula (II) to cyclic sulphates of formula (I) may be carried out, under particularly advantageous economic conditions, using a hypohalite (eg hypochlorite or hypobromite) of an alkali or alkaline earth metal, preferably sodium, potassium or calcium hypochlorite, in the presence of a catalytic quantity of a ruthenium derivative, preferably ruthenium (IV) oxide ($RuO_2$) or ruthenium chloride ($RuCl_3$).

The present invention is particularly useful for the preparation of cyclic sulphates of formula (I) in which n is 0 or 1 and $R_1$, $R_2$, $R_3$, $R_4$, $R_5$ and $R_6$ are identical or different and each represents hydrogen or alkyl of 1 to 4 carbon atoms which is unsubstituted or substituted by chlorine.

The new process may be carried out in an aqueous or two-phase aqueous-organic medium. When the process is carried out in a two-phase aqueous-organic medium the solvent is generally an optionally halogenated aliphatic or cycloaliphatic hydrocarbon, such as hexane, cyclohexane, methylene chloride, chloroform, carbon tetrachloride or dichloroethane, or an ester such as methyl acetate or ethyl acetate.

Generally, an excess of hypohalite is used relative to the sulphite of formula (II) employed. Preferably, 1 to 2 moles of hypohalite are used per mole of sulphite of formula (II).

Generally, a catalytic quantity of ruthenium derivative between $10^{-6}$ and $10^{-1}$ mole is used per mole of sulphite of formula (II).

The cyclic sulphate of formula (I) is separated from the reaction mixture by conventional methods.

The sulphite of formula (II) may be obtained by the known methods and in particular by the process described by D. S. Breslow and H. Skolnik, "The Chemistry of Heterocyclic Compounds—Multi-Sulphur and Sulphur and Oxygen 5-and 6-Membered Heterocycles", 1966, Part I, p.1 and Part II, p. 663 or by H. F. Van Woerden, Chem. Rev., 63, 557 (1963).

The following Examples illustrate the invention.

EXAMPLE 1

Ethylene sulphite (27 g, 0.25 mole), methylene chloride (175 cc) and ruthenium (IV) oxide dihydrate (18 mg, $0.106 \times 10^{-3}$ mole) are placed in a 250 cc round-bottomed flask. The mixture is cooled to 5° C., then a solution of sodium hypochlorite (2 moles per liter; 125 cc, 0.25 mole) is added with vigorous stirring in the course of 40 minutes.

Stirring is continued for 10 minutes at 5° C.

After decantaion, the organic phase is stirred with isopropanol (1 cc) for 10 minutes at 10° C., then it is washed with water (40 cc) at 5° C.

After concentrating the organic phase at 30° C. under reduced pressure (100 mm Hg; 13.3 kPa), ethylene sulphate (25.4 g, 0.205 mole) is obtained in the form of white crystals melting at 99° C.

The yield is 82%.

EXAMPLE 2

The same procedure is used as in example 1, but replacing the methylene chloride by methyl acetate.

Ethylene sulphate (24.3 g) is thus obtained in the form of white crystals melting at 99° C.

The yield is 78.2%.

EXAMPLE 3

Ethylene sulphite (13.5 g, 0.125 mole) and water (108 cc) are placed in a 250 cc round-bottomed flask. The mixture is cooled to 5° C., then a mixture of a solution of sodium hypochlorite (2 moles per liter; 62 cc, 0.137 mole) and ruthenium (IV) oxide dihydrate (9 mg, $0.053 \times 10^{-3}$ mole) is added with vigorous stirring in the course of 30 minutes. Stirring is continued for 10 minutes at 5° C. The precipitate obtained is separated by filtration and then washed with water (40 cc) at 5° C.

After drying at 20° C. for 17 hours under reduced pressure (10 mm Hg; 1.3 kPa), ethylene sulphate (10.4 g) is collected in the form of white crystals melting at 99° C.

The yield is 67%.

EXAMPLE 4

The same procedure is used as in example 3, but replacing the ruthenium (IV) oxide dihydrate by ruthenium chloride trihydrate ($RuCl_3.3H_2O$; 13.1 mg, $0.05 \times 10^{-3}$ mole).

Ethylene sulphate (10.6 g) is thus obtained in the form of white crystals melting at 99° C.

The yield is 68.4%.

EXAMPLE 5

Methylene chloride (250 cc), a solution of sodium hypochlorite (2.18 moles per liter; 50 cc) and ruthenium chloride trihydrate ($RuCl_3.3H_2O$; 0.15 g, $5.7 \times 10^{-4}$ mole) are mixed in a 1 liter round-bottomed flask. The mixture is cooled to 5° C., then propylene sulphite (73.2 g, 0.6 mole) and a solution of sodium hypochlorite (2.18 moles per liter; 300 cc) are added simultaneously at 5° C., in the course of 40 minutes. Stirring is continued for 25 minutes at 5° C. and then isopropanol (2 cc) is added and the mixture stirred for 20 minutes.

After decantation, the aqueous phase is extracted with methylene chloride ($2 \times 100$ cc). The organic phases are combined and washed with water (200 cc) at 5° C. and then dried over magnesium sulphate. After filtration and evaporation of the solvent under reduced pressure (20 mm Hg; 2.6 kPa), propylene sulphate (72 g) is obtained in the form of a light yellow oil whose b.p. is 80° C. under 1 mm Hg (0.13 kPa).

The yield is 87%.

EXAMPLE 6

1,2-Dimethylethylene sulphite (9.00 g, 0.066 mole), dichloromethane (90 cc) and ruthenium oxide dihydrate ($RuO_2.2H_2O$; $7 \times 10^{-3}$ g, $0.041 \times 10^{-3}$ mole) are placed in a round-bottomed flask equipped with a stirrer. The mixture is cooled to 5° C., then a solution of sodium hypochlorite (2.1 moles/liter; 35 cc, 0.073 mole) is added with vigorous stirring in the course of 40 minutes.

The two-phase mixture is stirred at 5° C. for a further 10 minutes. After decantation, the organic phase is stirred with isopropanol (0.5 cc) at 5° C. for 10 minutes, then washed with iced water (50 cc).

After concentrating the organic phase at 40° C. under reduced pressure (100 mm Hg; 13.3 kPa), an oil (7.0 g) is obtained whose assay by infra-red spectrum shows it to consist of 1,2-dimethylethylene sulphate (80%) and 1,2-dimethylethylene sulphite (20%) in the form of oil.

The yield is 57%.

EXAMPLE 7

1-Chloromethylethylene sulphite (8.00 g, 0.051 mole), dichloromethane (80 cc) and ruthenium chloride trihydrate (10 mg, $0.38 \times 10^{-4}$ mole) are placed in a round-bottomed flask equipped with a stirrer. The mixture is cooled to 5° C., then a solution of sodium hypochlorite (2.2 moles/liter; 25 cc, 0.055 mole) is run in, in the course of 40 minutes. Stirring is continued for 10 minutes at 5° C.

After decantation, isopropanol (2 cc) is added to the organic phase, which is then stirred for 10 minutes at 5° C. The mixture is washed with water ($3 \times 50$ cc). After concentrating the organic phase at 40° C. under reduced pressure (100 mm Hg; 13.3 kPa) an oil (2.40 g) is obtained whose assay by infra-red spectrum shows it to contain 27% of 1-chloromethylethylene sulphate. The yield is 8%.

1-Chloromethylethylenesulphate is a new compound. Its infra-red spectrum, determined in dichloromethane, shows principal characteristic absorption bands at 1398, 1214, 891, 651 and 535 cm$^{-1}$. Its mass spectrum shows: e.i. (electronic ionization):

M/Z(%):172(8), 123(100), 137(5) c.i. (chemical ionization ($NH_3$)): M/Z (%):190(15), 207(100).

Its proton nuclear magnetic resonance spectrum (at 200 MHz, in deuterated chloroform, displacement in ppm; HMDS reference standard):3.8 (d; —$CH_2Cl$); 4.7 (multiplet doublet, $CH_2$); 5.1 (m, CH).

EXAMPLE 8

2,2-Dimethylpropylene sulphite (8.00 g, 0.053 mole), dichloromethane (50 cc) and ruthenium oxide dihydrate ($RuO_2.2H_2O$; 9.3 mg) are placed in a round-bottomed flask equipped with a stirrer. The mixture is cooled to 5° C., then a solution of sodium hypochlorite (2.2 moles/liter) (24 cc) is added in the course of 40 minutes. Stirring is maintained for 20 minutes at 5° C.

After decantation, isopropanol (2 cc) is added to the organic phase and the mixture is stirred for 10 minutes at 5° C. the mixture is washed with water (50 cc), decanted and the organic phase dried over sodium sulphate. After concentrating at 45° C. under reduced pressure (100 mm Hg; 13.3 kPa), a mixture (3.9 g) is obtained whose assay by infrared spectrum shows it to consist of 2,2-dimethylpropylene sulphate (55%) and 2,2-dimethylpropylene sulphite (45%).

The yield is 24%.

EXAMPLE 9

2,2-Dimethylpropylene sulphite (8.00 g, 0.053 mole), water (40 cc) and ruthenium oxide dihydrate ($RuO_2.2H_2O$; 9.3 mg) are placed in a round-bottomed flask equipped with a stirrer. The mixture is cooled to 5° C., then a solution of sodium hypochlorite (2.2 moles/liter) (24 cc) is added in the course of 60 minutes. Stirring is maintained for 1 hour 30 minutes at 5° C. The precipitate obtained is separated by filtration, then washed with ice-water.

After drying at 20° C. for 12 hours under reduced pressure (10 mm Hg; 1.33 kPa), 2,2-dimethylpropylene sulphate (5.3 g) is recovered, melting at 77° C.

The yield is 60%.

| Elementary analysis: | | | | |
| --- | --- | --- | --- | --- |
| % calculated | C 36.15 | H 6.02 | O 38.53 | S 19.30 |
| % found | 35.76 | 6.32 | 38.66 | 19.05 |

EXAMPLE 10

Tetramethylethylene sulphite (2.1 g), water (20 cc) and ruthenium oxide dihydrate (2.5 mg) are placed in a round-bottomed flask equipped with a stirrer. The mixture is cooled to 15° C. and a solution of sodium hypochlorite (2.2 moles/liter; 6.4 cc) is added in the course of 45 minutes. Stirring is maintained for 1 hour at 15° C. The precipitate is recovered by filtration, then washed with water (10 cc) at 15° C.

After drying for 18 hours at 20° C. under reduced pressure (10 mm Hg; 1.33 kPa), tetramethylethylene sulphate (0.6 g) is obtained.

The yield is 24%.

| Elementary analysis: | | | | |
|---|---|---|---|---|
| % calculated | C 40.01 | H 6.60 | O 35.53 | S 17.80 |
| % found | 38.90 | 6.70 | 35.65 | 17.56 |

EXAMPLE 11

3-Chloro-propane-1,2-diol sulphite (4.96 g, 0.03 mole) and water (25 cc) are placed in a 250 cc round-bottomed flask. The mixture is cooled to 0° C., and a solution of sodium hypochlorite (2 mole/liter, 22.5 cc, 0.045 mole) containing ruthenium (IV) oxide dihydrate (4.5 mg, 0.027 mole) is added with stirring. Stirring is continued for two minutes at 2° C. The reaction mixture is extracted with dichloromethane (2×20 cc) and the organic phase obtained is treated with isopropanol (0.5 cc) and then washed with water (15 cc).

The organic phase obtained is dried and concentrated under reduced pressure (2 mm. Hg; 0.47 kPa). 3-Chloro-propane-1,2-diol sulphate (or 1-chloromethylethylene-sulphate) (3.95 g) is obtained as a colorless liquid.

We claim:
1. 1-Chloromethylethylene sulphate.

* * * * *